(12) United States Patent  
DeToro et al.

(10) Patent No.: US 7,662,119 B2  
(45) Date of Patent: Feb. 16, 2010

(54) MULTIPLE FUNCTION RATCHETING ORTHOTIC DEVICE

(75) Inventors: William W. DeToro, Poland, OH (US); Brian S. Perala, Warren, OH (US); William A. DeToro, Poland, OH (US); Jack N. Huey, Poland, OH (US)

(73) Assignee: Anatomical Concepts, Inc., Poland, OH (US)

( * ) Notice: Subject to any disclaimer, the term of this patent is extended or adjusted under 35 U.S.C. 154(b) by 8 days.

(21) Appl. No.: 12/220,078

(22) Filed: Jul. 21, 2008

(65) Prior Publication Data

US 2010/0016772 A1    Jan. 21, 2010

(51) Int. Cl.  
*A61F 5/00* (2006.01)

(52) U.S. Cl. .............................. 602/16; 602/20; 602/23

(58) Field of Classification Search ..................... 602/5, 602/16, 20–23, 26–27; 128/882  
See application file for complete search history.

(56) References Cited

U.S. PATENT DOCUMENTS

| | | |
|---|---|---|
| 183,376 A | 10/1876 | Darrach |
| 1,257,297 A | 2/1918 | Brown |
| 1,851,241 A | 3/1932 | Dresser |
| 2,516,253 A | 7/1950 | Pieterick |
| 2,559,473 A | 7/1951 | Slodek, Sr. |
| 2,591,373 A | 4/1952 | Petruch |
| 2,943,622 A | 7/1960 | Nelson |
| 3,026,869 A | 3/1962 | Peach |
| 3,669,105 A | 6/1972 | Castiglia |
| 3,779,654 A | 12/1973 | Horne |
| 3,923,047 A | 12/1975 | Chant |
| 4,337,764 A | 7/1982 | Lerman |
| 4,388,920 A | 6/1983 | Hajost et al. |
| 4,502,472 A | 3/1985 | Pansiera |
| 4,928,676 A | 5/1990 | Pansiera |
| 4,982,732 A | 1/1991 | Morris |
| 5,088,479 A | 2/1992 | DeToro |
| 5,135,469 A | 8/1992 | Castillo |
| 5,399,149 A | 3/1995 | Frankowiak et al. |
| 5,409,449 A * | 4/1995 | Nebolon ..................... 602/16 |
| 5,486,157 A | 1/1996 | DiBenedetto |
| 5,545,127 A | 8/1996 | DeToro |
| 5,624,389 A | 4/1997 | Zepf |
| 5,707,347 A | 1/1998 | Bixler |
| 5,776,086 A | 7/1998 | Pansiera |

(Continued)

*Primary Examiner*—Michael A. Brown  
(74) *Attorney, Agent, or Firm*—Robert J. Herberger

(57) ABSTRACT

An orthotic device for a joint of a human body at which a body appendage pivots includes a first member able to extend along a posterior portion of the appendage on a first side of the joint and a second member able to extend along a posterior portion of the appendage on a second side of the joint opposite the first side. A connection joining the first member and the second member provides a series of defined positions spaced angularly about an axis at which positions the connection can be alternately locked and released, allows pivoting, selective ratcheting and positioning of the second member relative to the first member about the axis, and can restrict pivoting of the second member relative to the first member within a desired angular range of motion. Notably, this orthotic device uniquely combines multiple joint functions into one convenient device which allows it to be used at different stages of therapy without being replaced or requiring additional equipment.

19 Claims, 7 Drawing Sheets

U.S. PATENT DOCUMENTS

| | | | |
|---|---|---|---|
| 5,814,000 A * | 9/1998 | Kilbey .................. 602/16 |
| 5,848,979 A | 12/1998 | Bonutti et al. |
| 5,873,847 A | 2/1999 | Bennett et al. |
| 5,908,398 A | 6/1999 | DeToro |
| 5,954,677 A * | 9/1999 | Albrecht et al. ............... 602/16 |
| 5,954,678 A | 9/1999 | Cruz |
| 6,045,520 A | 4/2000 | Buckley |
| 6,090,057 A | 7/2000 | Collins et al. |
| 6,113,562 A | 9/2000 | Bonutti et al. |
| 6,245,034 B1 | 6/2001 | Bennett et al. |
| 6,302,858 B1 | 10/2001 | DeToro et al. |
| 6,350,246 B1 | 2/2002 | DeToro et al. |
| 6,375,632 B1 | 4/2002 | Albrecht et al. |
| 6,488,644 B1 | 12/2002 | Ostrom et al. |
| 6,533,741 B1 | 3/2003 | Lee et al. |
| 6,589,195 B1 | 7/2003 | Schwenn et al. |
| 6,793,638 B1 | 9/2004 | DeToro et al. |
| 6,821,261 B2 | 11/2004 | Doty et al. |
| 6,872,187 B1 * | 3/2005 | Stark et al. .................... 602/16 |
| 6,981,957 B2 | 1/2006 | Knecht et al. |
| 6,993,808 B1 | 2/2006 | Bennett et al. |
| 7,011,641 B1 | 3/2006 | DeToro et al. |
| 7,083,583 B2 | 8/2006 | Opahle et al. |
| 7,112,179 B2 | 9/2006 | Bonutti et al. |
| 7,112,181 B1 | 9/2006 | DeToro et al. |
| 7,122,016 B1 | 10/2006 | DeToro et al. |

* cited by examiner

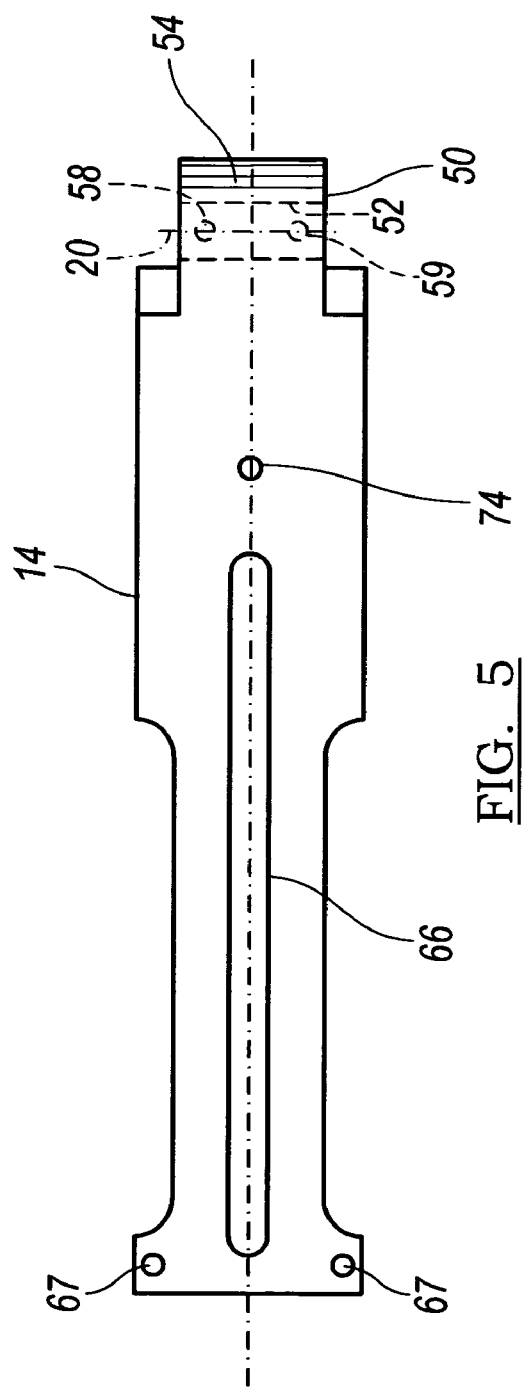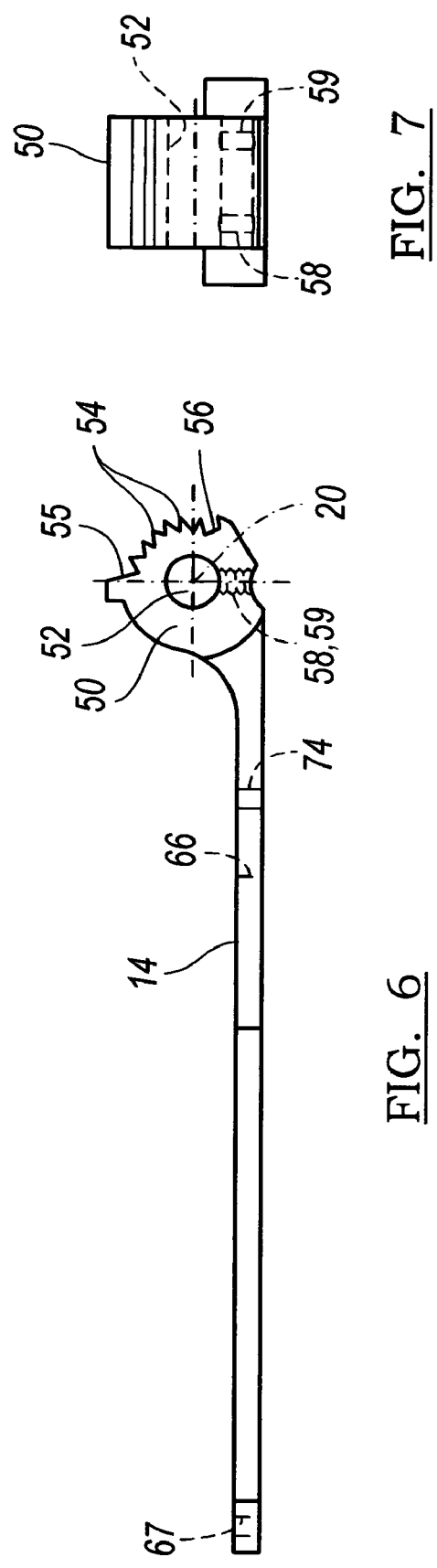

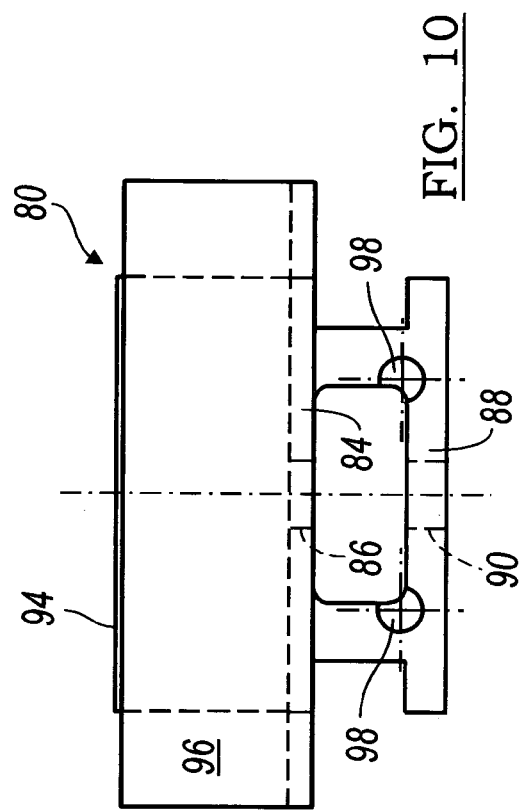
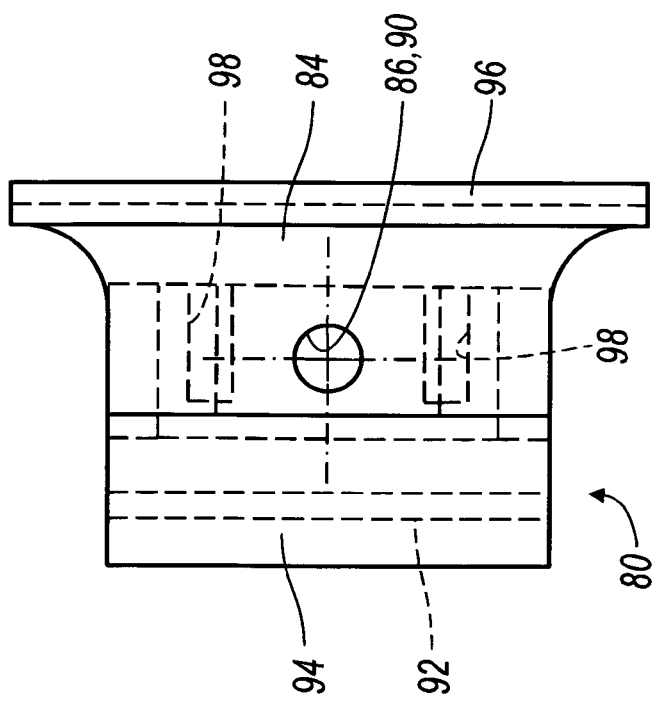
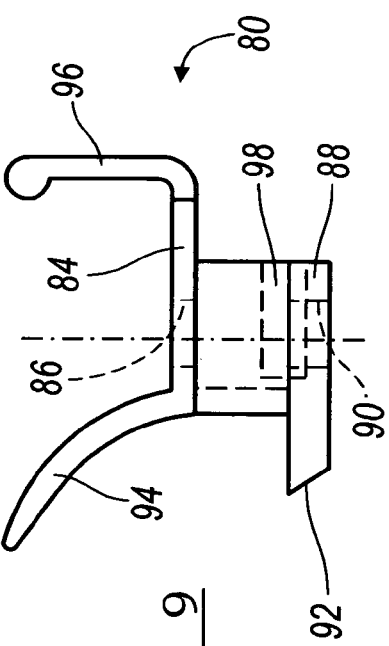

MULTIPLE FUNCTION RATCHETING ORTHOTIC DEVICE

BACKGROUND OF THE INVENTION

1. Field of the Invention

This invention relates generally to an orthotic device, and particularly to a leg brace that provides multiple, adjustable functions for controlling the angular position and motion of a knee.

2. Description of the Prior Art

An orthotic is a device, such as a brace or splint, for supporting, immobilizing, or treating muscles, joints, or skeletal parts, which are weak, ineffective, deformed, or injured. To assist in restoring a joint of the human body to normal, effective function, it may be preferred that the joint be restricted for a period by an orthotic, which imposes a fixed pivoted position. Or an orthotic may be needed that permits adjustable angular displacement of the joint, which is retained for a period by the orthotic and gradually increased at intervals to improve the pivotal range of use.

An orthotic leg device, for example, can typically provide one or two of five common functions: i) free motion about the knee joint as illustrated in U.S. Pat. Nos. 3,779,654 to Horne and 3,669,105 to Castiglia; ii) a ring drop lock joint to keep the knee joint extended as shown in U.S. Pat. Nos. 3,923,047 to Chant and 4,928,676 to Pansiera; iii) a step-lock ratchet joint to support the strength of the knee as it extends to various angular positions as seen in U.S. Pat. Nos. 4,502,472 and 5,776,086 to Pansiera; iv) a range of motion joint as disclosed in U.S. Pat. Nos. 4,337,764 to Lerman and 4,982,732 to Morris; or v) a variable, fixed position joint that can be locked in select positions as seen in U.S. Pat. Nos. 4,388,920 to Hajost et al. and 7,122,016 to DeToro et al. Each of these five different functioning knee braces has a specific use during therapy of a patient. In each case, a different brace is typically required.

A need exists, therefore, for one orthotic device that provides these multiple functions, including: a fixed position by releasing an attachment, changing the angular displacement of the orthotic about the axis to a new, desired orientation, and securing the orthotic to that desired position; a limited range of movement about the axis that can be adjusted easily and remain limited reliably by mutual contact between stop surfaces located on opposite sides of the axis; and a free range of movement about an axis. Further, an orthotic device that can be adjusted to multiple, mutually spaced ratcheted locations to enhance the range of flexibility and use of the joint provides an added advantage.

SUMMARY OF THE INVENTION

An orthotic device for a joint of the human body at which a body appendage pivots includes a first member able to extend along a posterior portion of the appendage on a first side of the joint and a second member able to extend along a posterior portion of the appendage on a second side of the joint opposite the first side. A connection joining the first member and the second member provides a series of defined positions spaced angularly about an axis at which positions the connection can be alternately locked and released, allows pivoting, selective ratcheting and positioning of the second member relative to the first member about the axis, and/or allows pivoting of the second member relative to the first member within a desired angular range of motion.

When the leg is contracted, the ratchet will lock in angular increments and stop re-contracture until the leg reaches the straight position, whereupon the brace prevents contracture and extension (i.e. step-lock ratchet function).

If the ratchet function is released, the leg can be contracted at the knee. More specifically, the ratcheting function can be locked out temporarily, such as when the person using the brace wishes to sit down. Notably, the ratchet re-engages automatically when the brace is fully extended, or it re-engages manually by applying slight upward pressure on the ratchet when in the locked out position (i.e. drop lock function).

By disengaging the ratchet completely, the joint of the orthotic device can turn freely about the lateral axis upon loosening lock nuts (i.e. free motion function).

Further, the brace can the adjusted to provide a range of pivoting motion about the joint by adjusting locknuts a predetermined amount corresponding to the desired flexion limit angle. The flexion limit angle is set first by adjusting the flexion limiting lock nut, and an extension angular limit is set by tightening or loosening the other lock nut (i.e. range of motion function). Further yet, the brace can be returned to the free motion function upon completely loosening both lock nuts, or the brace can be locked in any position by placing the brace in the desired angular flexion and tightening both lock nuts (i.e. variable, fixed position function).

Still further, the brace accommodates contraction and expansion of the muscles and skin that accompany flexion and extension of the knee joint, by providing an upper member having a thigh cuff attachable to the thigh that slides in an upper pocket, a lower member having a calf cuff attachable to the calf that slides in a lower pocket, so that the positions of the thigh and calf cuffs remain unchanged relative to the extension and contraction of the leg. The position of the joint, therefore, remains unchanged at the back of the knee due to the tendency of the springs to keep the brace cuffs at their secured positions.

The scope of applicability of the preferred embodiment will become even more apparent from the following detailed description, claims and drawings. It should be understood, that the description and specific examples, although indicating the preferred embodiments of the invention, are given by way of illustration only. Various changes and modifications to the described embodiments and examples will become apparent to those skilled in the art.

DESCRIPTION OF THE DRAWINGS

Having generally described the nature of the invention, reference will now be made to the accompanying drawings used to illustrate and describe the preferred embodiments thereof. Further, these and other advantages will become apparent to those skilled in the art from the following detailed description of the embodiments, when considered in the light of these drawings in which:

FIG. 5 is a top view of a lower member of the orthotic device of FIG. 1;

FIG. 6 is a side view of the lower member of FIG. 5;

FIG. 7 is an end view of the lower member of FIG. 5;

FIG. 9 is a side view of the ratchet of FIG. 8;

FIG. 10 is a front view of the ratchet of FIG. 8;

FIG. 11 is a top view of the ratchet of FIG. 8;

DESCRIPTION OF THE PREFERRED EMBODIMENT

Figure 1:
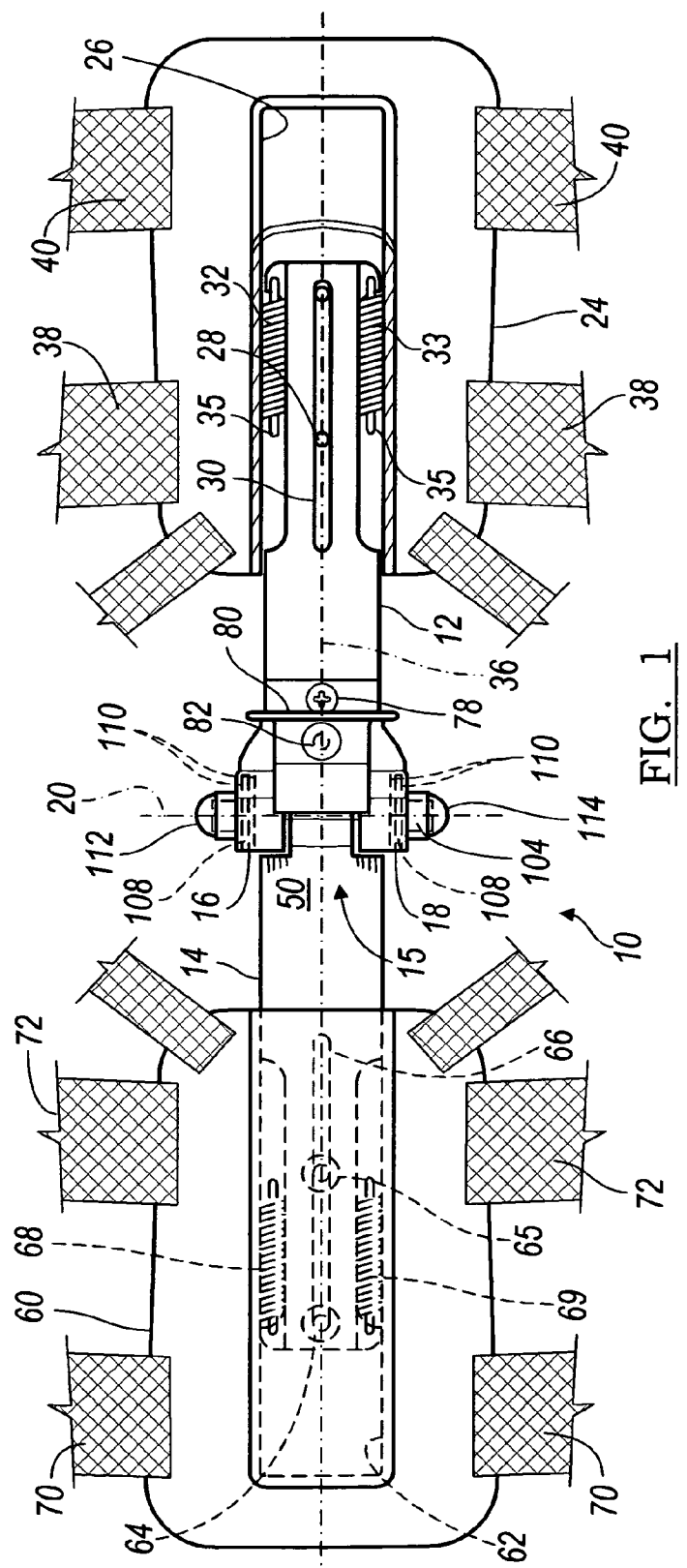
FIG. 1 is a rear view of a multiple function leg orthotic device.

Referring first to FIGS. 1 through 4, an orthotic device 10 includes an upper member 12 and a lower member 14, which are interconnected by a ratcheting joint 15. Each member 12, 14 is preferably formed of aluminum or another structural material having density, strength and endurance comparable to those of aluminum.

The upper member 12 includes two lugs 16, 18, spaced mutually along a lateral axis 20, each lug having a hole 22, 23, in which screw threads are tapped. Preferably, the screw threads in holes 22, 23 are right-hand threads. The outer surface of each lug 16, 18 is counterbored at the respective hole. A plastic thigh cuff 24, whose front surface conforms to the contour of the back of the human thigh, is formed at its back surface with a longitudinal pocket 26. The upper member 12 is inserted into pocket 26 and retained there by threaded attachments 28, each attachment comprising a screw which passes through a slotted hole 30 in member 12 and a nut that engage the screw and contacts the outer surface of pocket 26. Tension springs 32, 33, each have an end secured to the upper member 12 by engaging a hole 34, and the opposite end secured to the thigh cuff 24 at attachment element 35, thereby permitting member 12 to move elastically along an longitudinal axis 36 relative to the thigh cuff 24. Multiple velcro straps 38, 40 secure the thigh cuff 24 to the leg of the person wearing the brace 10. A threaded hole 42 is tapped in the upper member 12, and an elongated hole 44 is formed at a lower elevation than that of the threaded hole 42. The lower edge 46 of the upper member 12 faces the lower member 14.

Referring now to FIGS. 1 and 5 through 8, the lower member 14 includes: a central lug 50 located between lugs 16, 18 and formed with an unthreaded hole 52, which is aligned with lateral axis 20 and threaded holes 22, 23; a series of ratchet teeth 54, spaced mutually about axis 20; a stop surface 55; and a slot 56. Two tapped holes 58, 59, directed toward axis 20, are formed in lug 50. A calf cuff 60, whose front surface conforms to the contour of the calf of the human leg, is formed at its back surface with a longitudinal lower pocket 62. The lower member 14 is inserted into pocket 62 and retained there by threaded attachments 64, 65, each attachment comprising a screw which passes through a slotted hole 66 in member 14 and a nut that engage the screw and contacts the outer surface of pocket 62. Tension springs 68, 69, each have one end secured to the lower member 14 by engaging a hole 67, and the opposite end secured to the calf cuff 60, permitting member 14 to move along longitudinal axis 36 relative to the calf cuff 60. Multiple velcro straps 70, 72 secure calf cuff 60 to the patient's leg. A hole 74 is drilled in the lower member 14 to lock the cuff in a shortened position if necessary.

Figure 8:
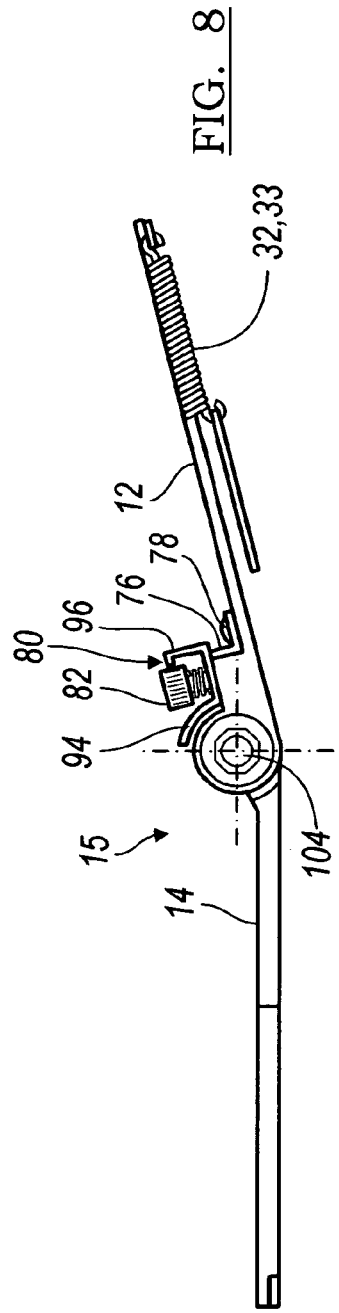
FIG. 8 is a side view of the joint that includes the upper and lower members and a ratchet.
Figure 2:
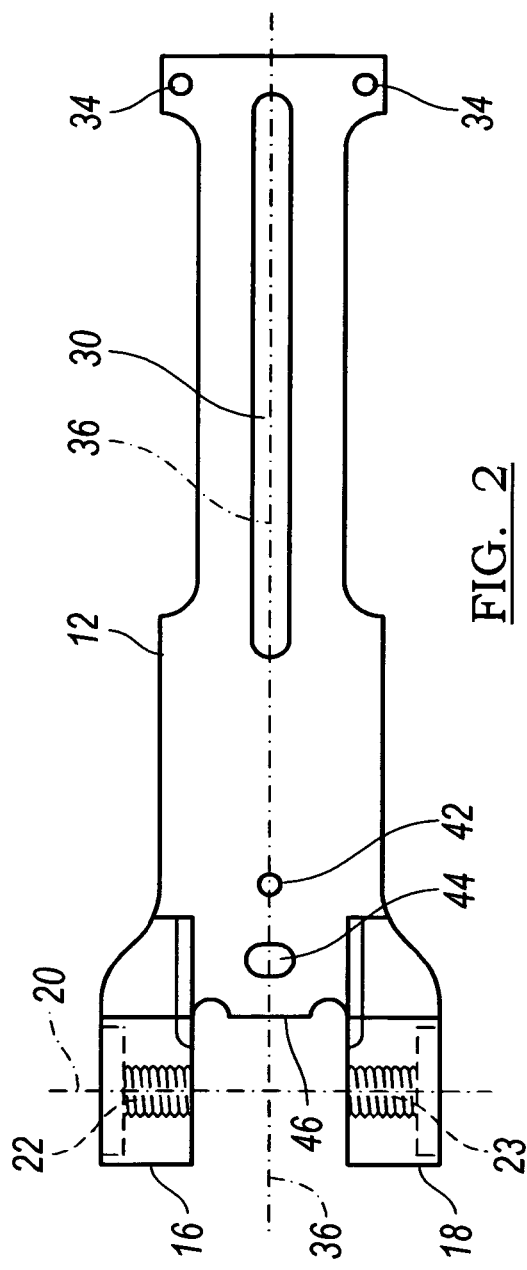
FIG. 2 is a top view of an upper member of the orthotic device of FIG. 1.
Figure 3:
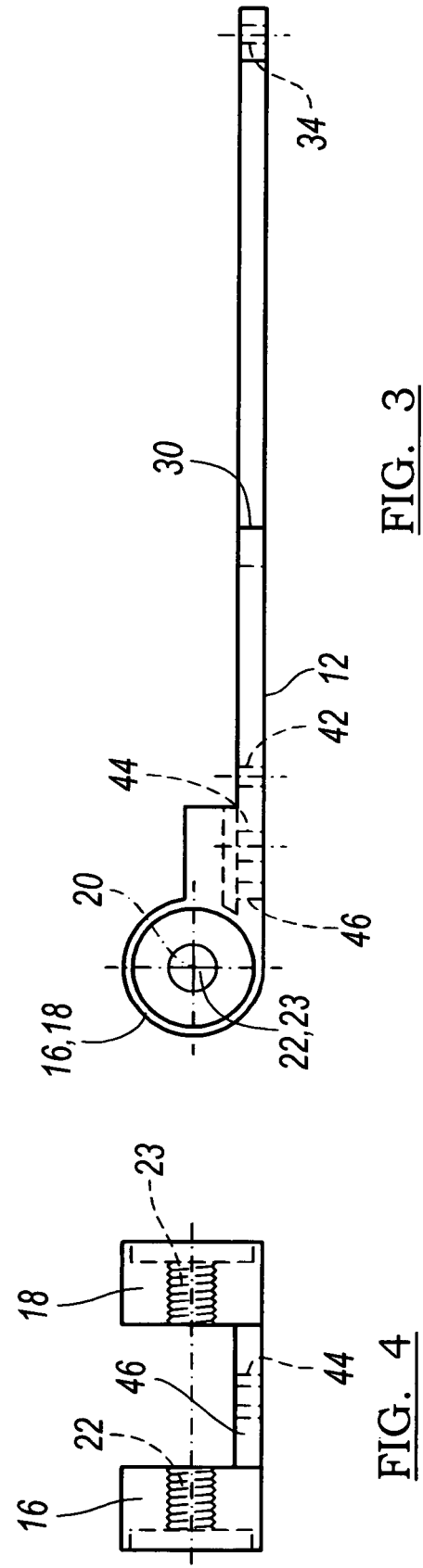
FIG. 3 is a side view of the upper member of FIG. 2.
Figure 4:
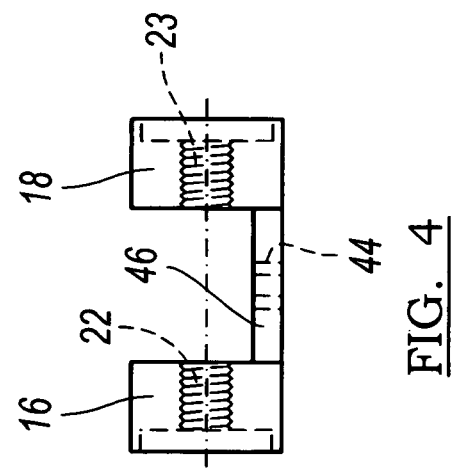
FIG. 4 is an end view of the upper member of FIG. 2.

FIGS. 1 and 8 show that the ratcheting joint 15 for connecting the upper member 12 and lower member 14 includes an angle stop bracket 76 secured to the upper member 12 by a screw 78 engaged in threaded hole 42, a ratchet 80, and a spring-loaded ratchet lockout pin 82 for securing the ratchet to the upper member 12.

FIGS. 8 through 12 illustrate details of the ratchet 80, which includes an upper plane 84 formed with an unthreaded hole 86; a lower plane 88 formed with an unthreaded hole 90, aligned with hole 86; and a latch 92 for engaging alternately the ratchet teeth 54, stop surface 55, and slot 56 on the lower member 14. A curved arm 94, located at the lower end of the upper plane 84, overlaps the ratchet teeth 54 to protect against an otherwise pinching-point. An adjustment arm 96, located at the upper end of plane 84, provides a surface with which to manually slide ratchet 80 along axis 36 away from the ratchet teeth 54. The ratchet includes two laterally spaced holes 98 directed parallel to axis 36 and closed at their lower ends, each hole 98 containing a compression spring 100. The leg of angle stop bracket 76 bears against one end of springs 100, urging latch 92 toward lug 50 and the ratchet teeth 54.

The spring-loaded ratchet lockout pin 82 is biased outward from holes 86 and 90 by a spring 101, fitted between the head of pin 82 and the outer surface of plane 84. A portion of the shank of pin 82 extends through spring 101 and the aligned holes 86, 90 in the ratchet 80. The threaded shank of pin 82 engages a floating nut 103, which is retained in a space between plane 84 and springs 100 such that the nut 103 cannot rotate when pin 82 is rotated.

Ratchet 80 can be moved manually upward along axis 36 against the force of springs 100 to a point where holes 86 and 90 in the ratchet become aligned with hole 44 in the upper member 12. When the ratchet 80 is in that position, it can be more permanently retained there by rotating pin 82 relative to nut 103, thereby driving and securing its shank against the force of spring 101 into elongated hole 44. Ratchet 80 is retained in that position due to contact between the shank of pin 82 and the surface of hole 44. When ratchet 80 is in that position, the ratchet is locked out, i.e., preventing engagement of latch 92 with the ratchet teeth 54 and slot 56 to allow free motion.

The force of springs 100 continually biases ratchet 80 downward toward engagement with the ratchet teeth 54. Ratchet 80 can be returned to the ratcheting position from the lockout position by rotating pin 82 in the opposite direction sufficiently to disengage its shank from nut 103, whereupon ratchet 80 is forced elastically to the ratcheting position by the force of springs 100, i.e. step lock function.

It is important to note that ratchet 80 can be placed temporarily in the lockout position by aligning holes 86, 90 in the ratchet with hole 44 in the upper member 12. Then, without rotating the pin 82 relative to floating nut 103, pin 82 and nut 103 are pushed against the force of spring 101 into hole 44, where ratchet 80 is retained by a frictional reaction force between the shank of pin 82 and the surface of elongated hole 44 due to the force of springs 100.

Figure 12:
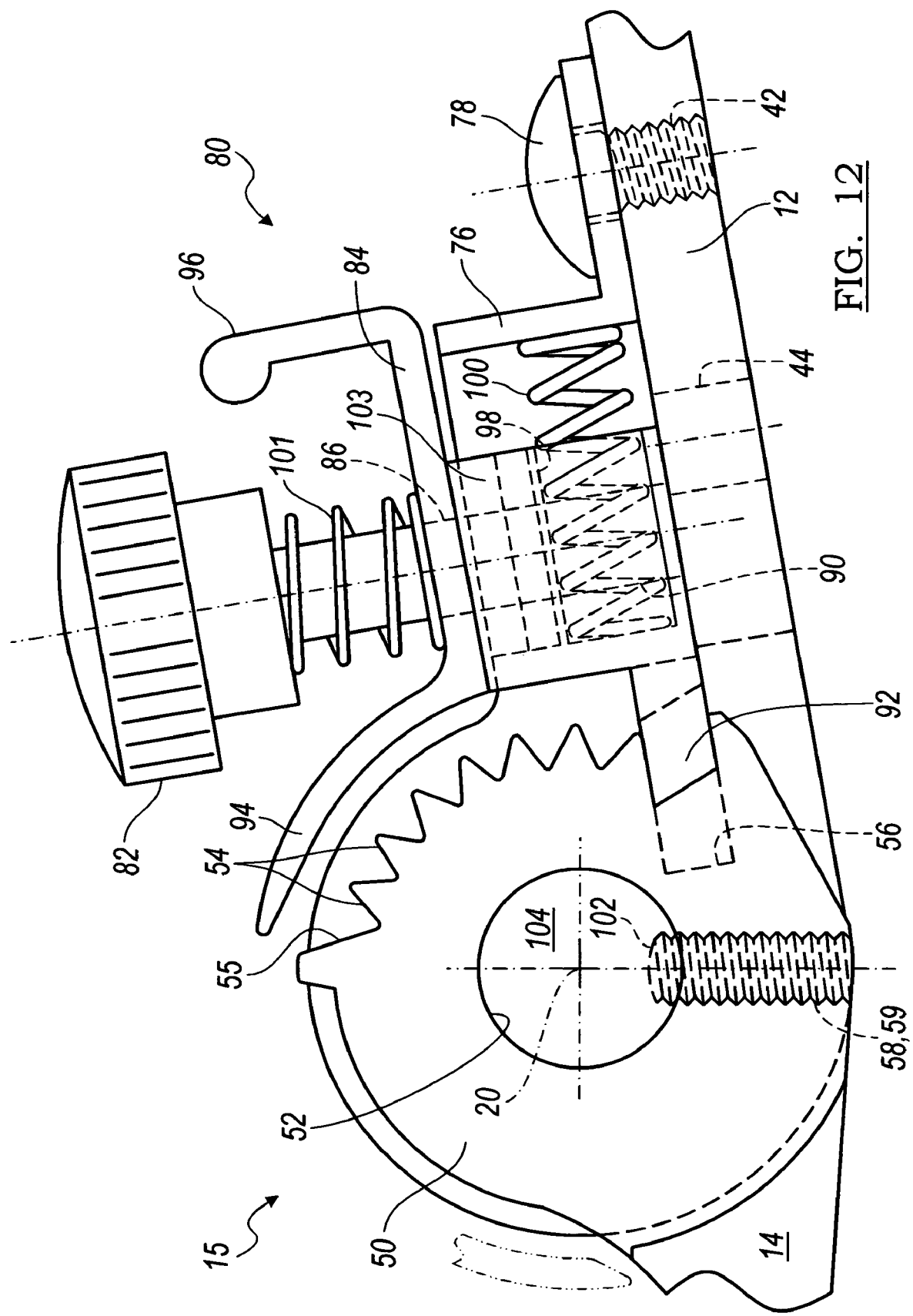
FIG. 12 is a side view of the ratchet joint that connects the upper and lower members.

In summary, therefore, with view of FIG. 12, the shank of ratchet lockout pin 82 is engaged with nut 103 and the holes 86, 90 of ratchet 80. The ratchet is moved upward along axis 36 in opposition to the force of springs 100 to the ratchet lock out position, where pin 82 enters the elongated hole 44 in the upper member 12. In the ratchet lock out position, latch 92 is disengaged from ratchet teeth 54 and slot 56 on the lower member 14. Upon moving pin 82 out of hole 44, ratchet 80 is forced downward by springs 100 such that latch 92 ratchets on or engages with the ratchet teeth 54, or engages the stop surface 55 or enters the slot 56 on lug 50 of the lower member 14.

Further, FIG. 12 shows a set screw 102 threaded into hole 58 and engaged with the shank of a headless bolt 104, whose right-hand screw threads are engaged with the threaded holes 22, 23 in lugs 16, 18, respectively, of the upper member. Bolt 104 passes through the unthreaded hole 52 in the lug 50 of the lower member 14. A similar set screw 102 is threaded into hole 59 and engaged with bolt 104. The set screws 102 prevent rotation of bolt 104 relative to lug 50 about axis 20, so as to create axial rotation of bolt 104 along axis 20 in joint 15 by pivoting the lower member 14 relative to upper member 12.

Figure 13:
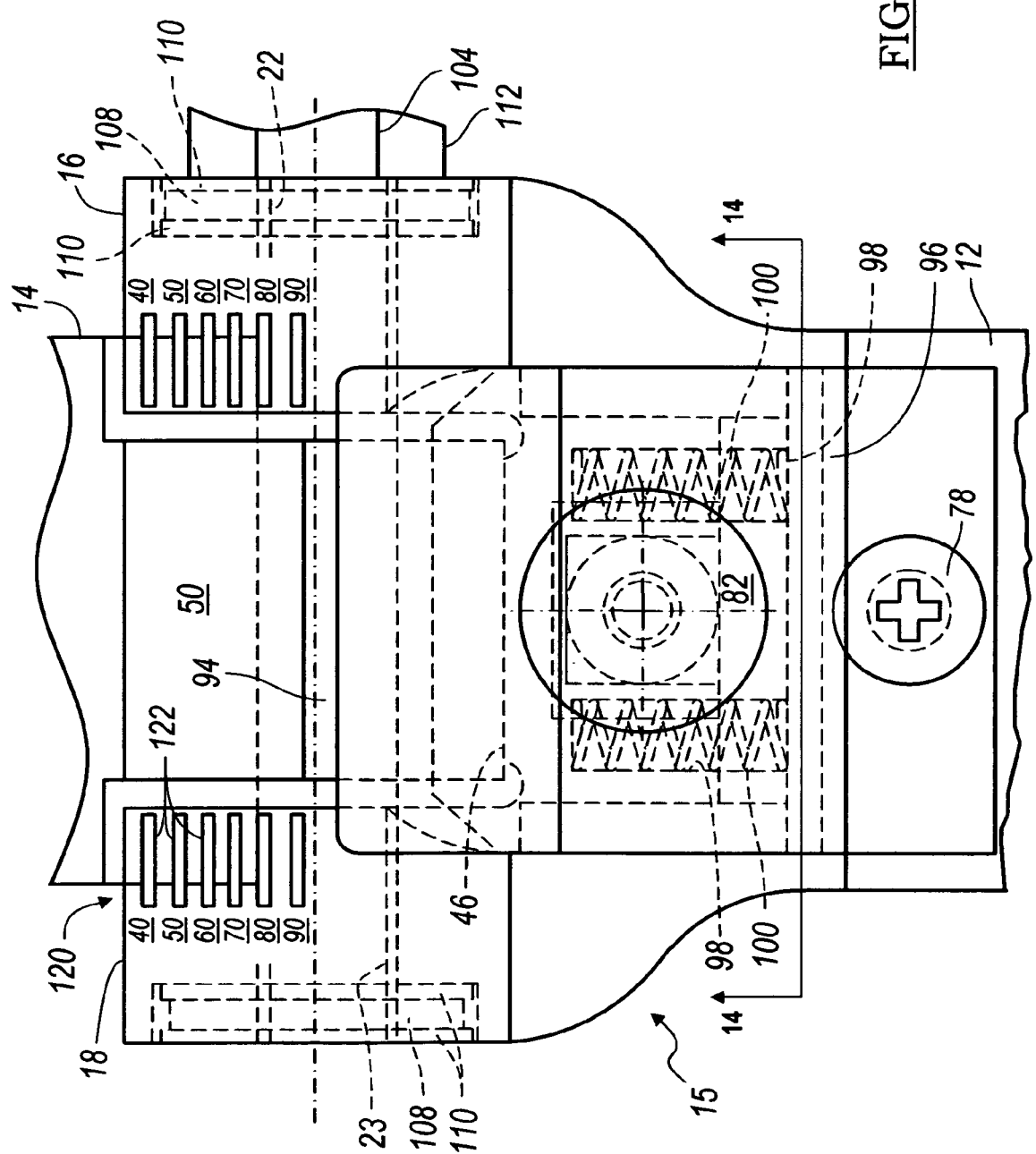
FIG. 13 is a top view of the ratchet joint of FIG. 12.
Figure 14:
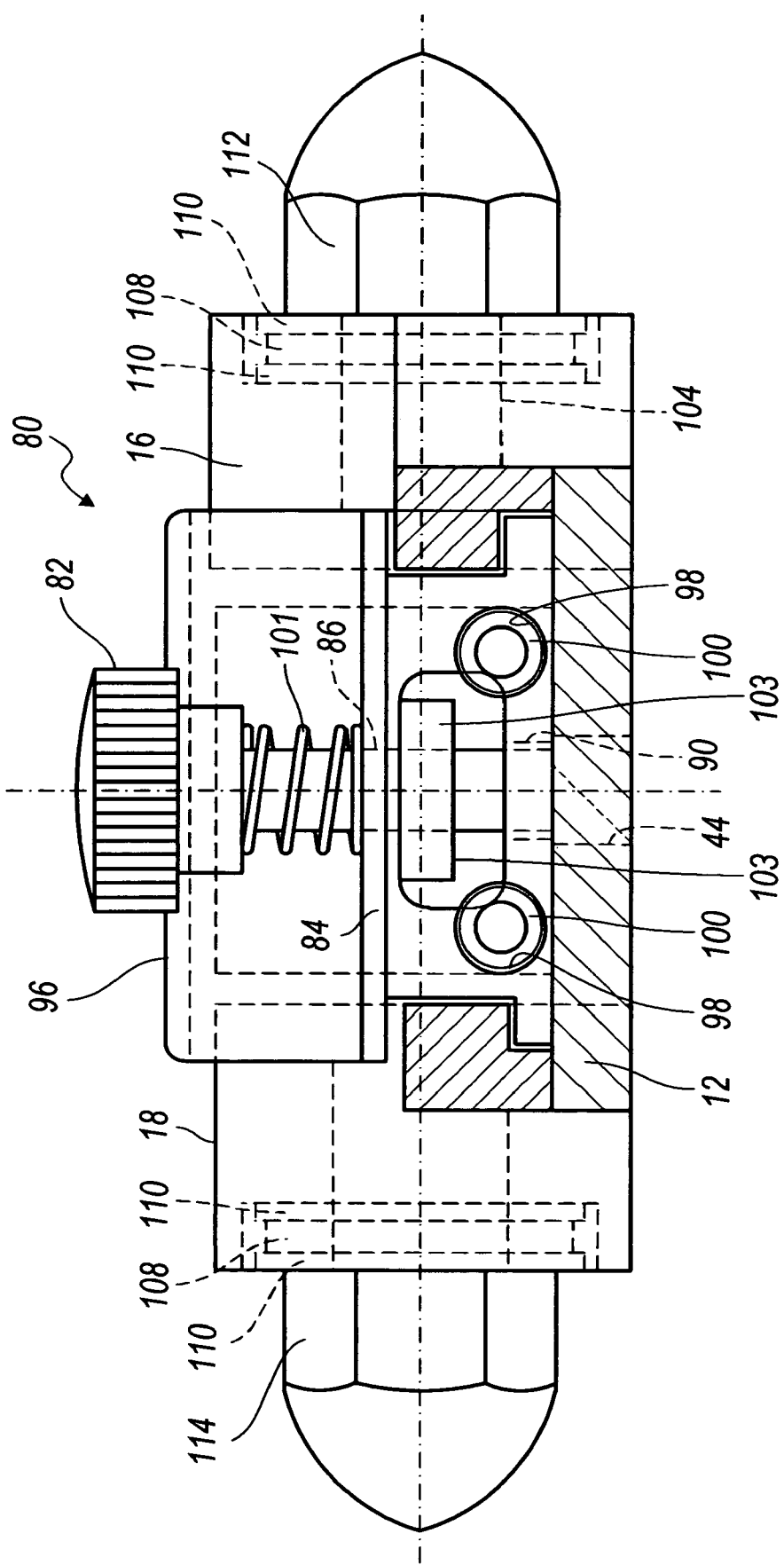
FIG. 14 is a cross section taken at plane 14-14 of FIG. 13.

Focusing now on FIGS. 1, 13 and 14, a thrust bearing 108 and washers 110, located on opposite sides of the thrust bearing, are fitted in the counterbore formed in the outer surface of lugs 16, 18 to facilitate loosening and tightening lock nuts 112, 114 on the threads of bolt 104.

As FIG. 13 illustrates, the surfaces of the lugs 16, 18 of the upper member 12 include a scale 120 of graduated angular positions or witness marks 122. The scaled witness marks 122 correspond to the angular displacement of the joint 15 from a reference angular position, i.e., the straight-out position of the leg, in which members 12 and 14 are aligned substantially parallel to axis 36. Latch 92 can engage the respective ratchet tooth 54 that corresponds to the selected angular position.

In operation, the joint 15 is able to pivot about the lateral axis 20 and the brace 10 can provide multiple functions, as described below:

1. To activate the ratchet 80, the ratchet lockout pin 82 is turned counterclockwise relative to nut 103 several revolutions until the ratchet releases. The ratchet 80 can be locked again by retracting ratchet 80 and turning the ratchet lockout pin 82 several turns clockwise.

To lock out the ratchet 80 on a temporary basis, such as when the person using the brace 10 is sitting down, ratchet 80 is retracted to the stop bracket 76 and the ratchet lockout pin 82 is pushed toward the back of the leg, which causes the shank of pin 82 to enter hole 44 where it is retained by the force of springs 100 in a friction hold position. Pin 82 is held in, thereby releasing ratchet 80. The ratchet 80 will lock automatically when the brace 10 returns to the straight position, i.e., the drop lock function. The ratchet 80 can also be reengaged by applying slight upward pressure on the ratchet to release the friction hold position.

2. When ratchet 80 is locked out on a temporary basis as described above, it will automatically release when slot 56 is contacted, slightly pushing latch 92, causing the shank of pin 82 to briefly move away from the wall of hole 44, whereby spring 101 forces upward the lock out pin 82 to disengage. Then, in the released position, the ratchet will automatically lock when the leg reaches the straight position, i.e. full extension. Once the ratchet is released from the temporary lockout position when the leg is contracted at the knee, the ratchet will lock and stop contracture every 10° to 20°, i.e. the distance between successive ratchet teeth, until the leg reaches the straight position, whereupon the brace 10 will not allow contracture or extension due to engagement of latch 92 in slot 56. Preferably, the distance between successive ratchet teeth corresponds to about 15°.

3. The joint 15 can rotate freely (i.e. free motion function) or be set to a particular range of motion (i.e. range of motion function), with or without ratcheting (which is described in more detail below) upon loosening or tightening lock nuts 112 and 114 about bolt 104. By adjusting the lock nuts 112, 114, the range of motion of brace 10 is changed about the lateral axis 20. More specifically, as upper member 12 rotates about bolt 104 (which is secured to lower member 14 by set screws 102 at center lug 50), lugs 16, 18 move up and down axis 20 by their threadable engagement with bolt 104 at threaded holes 22, 23, respectively, until either lug 16 contacts lock nuts 112 or lug 18 contacts lock nut 114. At that point, the range of motion stops.

By adjusting lock nuts 112 and 114 along bolt 104, the pivotal range of motion between lower member 14 and upper member 12 can be changed or locked to best accommodate the several stages of therapy. More specifically, with ratchet 80 locked out permanent or temporarily as described above, the brace 10 can be adjusted to provide a range of motion. With brace 10 in the straight position, both lock nuts 112, 114 are tightened. The joint 15 is then locked and allows no rotary movement about axis 20. If, for example, a flexion limit angle of 20° is desired, lock nut 112 is loosened, and the joint 15 can then be pivoted through an angle of approximately 20°, in the direction that reduces the magnitude of the angle between the thigh and the calf. The desired flexion limit angle can be checked with reference to the witness marks 122 located near the lock nuts 112, 114 on lugs 16, 18. Lock nut 112 can be adjusted to precisely set the desired flexion limit angle.

If a combination of flexion and extension is desired, the flexion limit angle is set first by adjusting lock nut 114, as described above. Then, the extension angular limit is set by tightening lock nut 112. The desired extension limit angle can be checked with reference to the witness marks 122 located near the lock nuts 112, 114 on lugs 16, 18. Lock nut 112 can be adjusted to precisely set the desired extension limit angle. The brace 10 is returned to the free motion function upon loosening both lock nuts 112, 114 about one-half turn.

4. The brace 10 can also be adjusted to select a desired angular position without pivoting in either direction. To accomplish this, lock nuts 112, 114 are loosened about one-half turn and, with ratchet 80 locked out permanent or temporarily as described above, joint 15 is pivoted about axis 20 to the desired angular position, and the lock nuts are retightened, thereby relocking joint 15 at the desired position (i.e. variable, fixed position function).

Finally, it is important to note that with this orthotic device being mounted to the posterior portion of an appendage, as the joint flexes, contraction of the muscles and skin occurs. Therefore, with this knee orthotic, for example, the thigh cuff 24 and calf cuff 60 are positioned and firmly secured by velcro straps 38, 40 and 70, 72, respectively, to the leg and back of the knee. In order to accommodate contraction and expansion of the muscles and skin that accompany flexion and extension of the knee joint, therefore, upper member 12 slides along axis 36 in upper pocket 26 and lower member 14 slides along the axis 36 in the longitudinal lower pocket 62, while the positions of the thigh cuff 24 and calf cuff 60 relative to the leg remain unchanged. As a result, the location of joint 15 remains unchanged at the back of the knee due to the tendency of springs 32, 33, 68, 69 to allow the thigh cuff 24 and calf cuff 60 to dynamically reposition relative to the joint 15.

It should be noted that the present invention can be practiced otherwise than as specifically illustrated and described, without departing from its spirit or scope. It is intended that all such modifications and alterations be included insofar as they are consistent with the objectives and spirit of the invention.

What is claimed is:

1. An orthotic device for a joint of a human body at which a body appendage pivots, comprising:
   a first member able to extend along a posterior portion of the appendage on a first side of the joint;
   a second member able to extend along a posterior portion of the appendage on a second side of the joint opposite the first side; and
   a connection joining the first member and the second member and providing at least one of a series of defined positions spaced angularly about an axis at which positions the connection can be alternately locked and released, and pivoting of the second member relative to the first member about the axis within a desired angular range of motion by adjusting a flexion limiting lock nut relative to an extension limiting lock nut on a bolt aligned with the axis.

2. The orthotic device of claim 1 wherein:
the connection alternately can be locked to prevent flexion of the appendage, and the connection permits flexion and extension of the appendage about the desired range of motion.

3. The orthotic device of claim 1 wherein the appendage is an arm and the joint is an elbow, and the first member extends along a forearm and the second member extends along an upper arm.

4. The orthotic device of claim 1 wherein the appendage is a leg and the joint is a knee, and the first member extends along a thigh and the second member extends along a calf.

5. An orthotic device for a joint of a human body at which a body part pivots, comprising:
a first member having a first member cuff able to extend along a first posterior portion of the body part on a first side of the joint;
a second member secured to the first member for pivoting about an axis, the second member having a second member cuff able to extend along a second posterior portion of the body part on a side of the joint opposite the first side, and the second member including ratchet teeth; and
a ratchet supported for movement relative to the ratchet teeth and including a latch, a spring for urging the latch toward engagement with the ratchet teeth, and a lockout pin for alternately securing the latch against movement toward engagement with the ratchet teeth and for releasing the latch to engage the ratchet teeth, wherein the lockout pin includes a shank that can engage the first member such that the latch is prevented from engaging the ratchet teeth to allow contracture of the joint.

6. The orthotic device of claim 5, further comprising:
mutually aligned adjuster holes formed on the ratchet, wherein the shank extends through the adjuster holes and the shank is formed with a screw thread; and
a lockout hole formed on the first member, engageable by the shank and located such that the latch is prevented from engaging the ratchet teeth when the shank extends into the lockout hole.

7. The orthotic device of claim 5, further comprising:
mutually aligned adjuster holes formed on the ratchet, wherein the shank extends through the adjuster holes and the shank is formed with a screw thread;
a nut engaged with the threads on the shank, retained on the ratchet and prevented from rotating when engaged by the shank; and
a lockout hole formed on the first member, engageable by the shank and located such that the latch is prevented from engaging the ratchet teeth when the shank extends into the lockout hole.

8. The orthotic device of claim 5, further comprising:
mutually aligned adjuster holes formed on the ratchet, wherein the shank extends through the adjuster holes and the shank is formed with a screw thread;
a nut engaged with the threads on the shank, retained on the ratchet and prevented from rotating when engaged by the shank;
a lockout hole formed on the first member, engageable by the shank and located such that the latch is prevented from engaging the ratchet teeth when the shank extends into the lockout hole; and
a second spring for urging the lockout pin away from engagement with the lockout hole.

9. The orthotic device of claim 5 wherein:
the first member further comprises a first lug having a first hole, a second lug spaced from the first lug and having a second hole aligned with the first hole;
the second member further comprises a third lug located between the first and second lugs, the third lug having ratchet teeth angularly spaced about the axis and a third hole aligned with the first and the second holes; and
the first member and the second member being interconnected at the lugs by a bolt having a screw thread that threadably engages the first hole and the second hole, the bolt extends through the third hole and the third lug is secured against rotation about the bolt, and first and second lock nuts engage the screw thread on opposite ends of the bolt for restricting rotation of the first and second lugs about the axis.

10. An orthotic device for a joint of a human body at which a body part pivots, comprising:
a first cuff including a first pocket that extends along a first posterior portion of the body part, the first cuff able to be secured to the first posterior portion of the body part on a first side of the joint;
a first member that extends into the first pocket, moves along the first pocket relative to the first cuff, and is urged elastically to return to a first reference position in the first pocket;
a second cuff including a second pocket that extends along a second posterior portion of the body part, the second cuff able to be secured to the second posterior portion of the body part on a second side of the joint opposite the first side;
a second member that extends into the second pocket, moves along the second pocket relative to the second cuff, is urged elastically to return to a second reference position in the second pocket, is secured to the first member for pivoting about an axis, and includes ratchet teeth; and
a ratchet supported for movement relative to the ratchet teeth and including a latch, a spring for urging the latch toward engagement with the ratchet teeth, and a lockout pin for alternately securing the latch against movement toward engagement with the ratchet teeth and for releasing the latch to engage the ratchet teeth.

11. The orthotic device of claim 10, further comprising:
mutually aligned adjuster holes formed on the ratchet, the lockout pin further includes a shank that extends through the adjuster holes, the shank being formed with a screw thread; and
a lockout hole formed on the first member, engageable by the shank and located such the latch is prevented from engaging the ratchet teeth when the shank extends into the lockout hole.

12. The orthotic device of claim 10, further comprising:
mutually aligned adjuster holes formed on the ratchet, the lockout pin includes a shank that extends through the adjuster holes, the shank being formed with a screw thread;
a nut engaged with the threads on the shank, retained on the ratchet and prevented from rotating when engaged by the shank; and
a lockout hole formed on the first member, engageable by the shank and located such the latch is prevented from engaging the ratchet teeth when the shank extends into the lockout hole.

13. The orthotic device of claim 10, further comprising:
mutually aligned adjuster holes formed on the ratchet, the lockout pin includes a shank that extends through the adjuster holes, the shank being formed with a screw thread;

a nut engaged with the threads on the shank, retained on the ratchet and prevented from rotating when engaged by the shank;

a lockout hole formed on the first member, engageable by the shank and located such the latch is prevented from engaging the ratchet teeth when the shank extends into the lockout hole; and a second spring for urging the pin away from engagement with the lockout hole.

14. The orthotic device of claim 10 wherein:

the first member further comprises a first lug having a first hole, a second lug spaced from the first lug and having a second hole aligned with the first hole;

the second member further comprises a third lug located between the first and second lugs, the third lug having ratchet teeth angularly spaced about the axis and a third hole aligned with the first and the second holes; and the first member and the second member being interconnected at the lugs by a bolt having a screw thread that threadably engages the first hole and the second hole, the bolt extending through the third hole and the third lug is secured against rotation about the bolt, and first and second lock nuts engage the screw thread on opposite ends of the bolt for limiting rotation of the first and second lugs about the axis.

15. An orthotic device for a joint of a human body at which a body part pivots, comprising:

a first cuff including a first pocket that extends along a first posterior portion of the body part, the first cuff able to be secured to the first posterior portion of the body part on a first side of the joint;

a first member that extends into the first pocket, moves along the first pocket relative to the first cuff, and is urged elastically to return to a first reference position in the first pocket;

a second cuff including a second pocket that extends along a second posterior portion of the body part, the second cuff able to be secured to the second posterior portion of the body part on a second side of the joint opposite the first side;

a second member that extends into the second pocket, moves along the second pocket relative to the second cuff, and is urged elastically to return to a second reference position in the second pocket; and a pivotal connection joining the first member and the second member and providing a series of defined positions spaced angularly about an axis at which positions the pivotal connection can be alternately locked and released by a ratchet, and first and second lock nuts to limit rotation of the first member and the second member about the axis within a desired angular range of motion.

16. The orthotic device of claim 15 wherein:

the connection alternately can be locked by the first and second lock nuts to prevent rotation.

17. A method for operating an orthotic device comprising the steps of:

securing a first member to a first posterior portion of a body part on a first side of a joint, the first member comprising a first lug having a first hole and a second lug spaced from the first lug having a second hole aligned with the first hole;

securing a second member to a second posterior portion of the body part on a second side of the joint opposite the first side, the second member comprising a third lug located between the first and second lugs, the third lug having ratchet teeth angularly spaced about an axis and a third hole aligned with the first and the second holes, the first member and the second member being interconnected at the lugs by a bolt having a screw thread that threadably engages the first and second holes, the bolt extending through the third hole and the third lug is secured against rotation about the bolt;

using a latch on the first member to engage the ratchet teeth located on the second member and spaced angularly about the axis; and locking the latch into engagement with a ratchet tooth at a desired angular position about the axis.

18. The method claim 17 further comprising the steps of:

disengaging the latch from the ratchet teeth;

securing the latch against automatic reengagement with the ratchet teeth; and adjusting first and second lock nuts at opposite ends of the bolt to permit the first member to pivot freely about the axis relative to the second member within a desired range of motion.

19. The method claim 17 further comprising the steps of:

disengaging the latch from the ratchet teeth;

securing the latch against automatic reengagement with the ratchet teeth; and tightening first and second lock nuts at opposite ends of the bolt to secure the first member from pivoting about the axis relative to the second member.

* * * * *